United States Patent
Su et al.

(10) Patent No.: US 10,667,673 B2
(45) Date of Patent: Jun. 2, 2020

(54) HANDHELD CATHETER DRIVER WITH ENDOSCOPE MOUNT UTILIZING FRICTION-DRIVEN WHEEL MECHANISM

(71) Applicant: KONINKLIJKE PHILIPS N.V., Eindhoven (NL)

(72) Inventors: Hao Su, Hartsdale, NY (US); Gregory Cole, Ossining, NY (US); Vijay Parthasarathy, Lexington, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 462 days.

(21) Appl. No.: 15/518,254

(22) PCT Filed: Oct. 10, 2015

(86) PCT No.: PCT/IB2015/057754
§ 371 (c)(1),
(2) Date: Apr. 11, 2017

(87) PCT Pub. No.: WO2016/063165
PCT Pub. Date: Apr. 28, 2016

(65) Prior Publication Data
US 2017/0303773 A1    Oct. 26, 2017

Related U.S. Application Data

(60) Provisional application No. 62/067,477, filed on Oct. 23, 2014.

(51) Int. Cl.
| A61B 1/00 | (2006.01) |
| A61B 34/30 | (2016.01) |
| A61B 1/018 | (2006.01) |

(52) U.S. Cl.
CPC ...... *A61B 1/00133* (2013.01); *A61B 1/00064* (2013.01); *A61B 34/30* (2016.02);
(Continued)

(58) Field of Classification Search
CPC . A61B 1/00133; A61B 1/018; A61B 1/00039; A61B 2034/301; A61B 2017/0034
See application file for complete search history.

(56) References Cited

U.S. PATENT DOCUMENTS

4,559,928 A    12/1985  Takayama
5,159,446 A *  10/1992  Hibino ............... A61B 1/00039
                                                      348/65
(Continued)

FOREIGN PATENT DOCUMENTS

| CN | 103239793 A | 8/2013 |
| JP | 57203657 | 12/1982 |
| WO | 2011008922 A2 | 1/2011 |

OTHER PUBLICATIONS

Nair, G.B. et al., "Ergonomics in bronchoscopy: is there a need for better design or a change in the work environment?" Expert Review of Respiratory Medicine 6.1 (2012): 1-2.

*Primary Examiner* — John P Leubecker

(57) ABSTRACT

An instrument driving mechanism includes an instrument drive assembly (140) including a first set of wheels (136) coupled to a first end portion and a second set (138) of wheels coupled to a second end portion opposite the first end portion. The first set of wheels is configured to engage an elongated instrument (104) therein such that a rotation plane of the first set of wheels is coplanar with a longitudinal axis of the instrument. The second set of wheels is configured to engage the elongated instrument therein such that a rotation plane of the second set of wheels is obliquely oriented with the longitudinal axis of the instrument wherein motion of the instrument is controlled by controlling rotations of the wheels. The instrument drive assembly mounts to a mounting position (149) of a medical device that permits the (Continued)

instrument to pass therethrough and is configured to fix a position of the instrument drive assembly to enable positioning of the instrument.

20 Claims, 6 Drawing Sheets

(52) U.S. Cl.
CPC ........... *A61B 1/00039* (2013.01); *A61B 1/018* (2013.01); *A61B 2034/301* (2016.02)

(56) References Cited

U.S. PATENT DOCUMENTS

| | | | | |
|---|---|---|---|---|
| 6,027,497 | A * | 2/2000 | Daniel | A61B 1/00098 606/15 |
| 7,524,284 | B2 | 4/2009 | Murakami | |
| 7,819,799 | B2 | 10/2010 | Merril | |
| 8,075,474 | B2 | 12/2011 | Honda et al. | |
| 8,870,815 | B2 | 10/2014 | Bhat et al. | |
| 9,486,124 | B2 | 11/2016 | Yamada | |
| 9,682,214 | B2 | 6/2017 | Schultz | |
| 9,775,677 | B2 | 10/2017 | Hyodo et al. | |
| 2003/0040737 | A1 | 2/2003 | Merril et al. | |
| 2006/0041245 | A1* | 2/2006 | Ferry | A61B 1/00133 604/510 |
| 2006/0161045 | A1* | 7/2006 | Merril | A61B 1/018 600/117 |
| 2006/0224162 | A1 | 10/2006 | Suzuki et al. | |
| 2006/0287667 | A1 | 12/2006 | Abela | |
| 2008/0294003 | A1* | 11/2008 | Honda | A61B 1/00071 600/114 |
| 2009/0018390 | A1* | 1/2009 | Honda | A61B 1/00059 600/106 |
| 2009/0105536 | A1* | 4/2009 | Honda | A61B 1/00133 600/106 |
| 2009/0118575 | A1* | 5/2009 | Ichikawa | A61B 1/00133 600/103 |
| 2009/0137872 | A1 | 5/2009 | Bahney | |
| 2009/0209812 | A1 | 8/2009 | Omoto | |
| 2009/0281378 | A1* | 11/2009 | Banju | A61B 1/00133 600/106 |
| 2010/0022825 | A1* | 1/2010 | Yoshie | A61B 1/00133 600/104 |
| 2010/0191050 | A1* | 7/2010 | Zwolinski | A61B 1/018 600/104 |
| 2011/0077591 | A1 | 3/2011 | Plicchi et al. | |
| 2012/0232476 | A1 | 9/2012 | Bhat et al. | |
| 2013/0096589 | A1 | 4/2013 | Spencer et al. | |
| 2014/0171735 | A1* | 6/2014 | Galperin | A61B 1/00066 600/106 |
| 2015/0045617 | A1 | 2/2015 | Yamada | |
| 2015/0164307 | A1* | 6/2015 | Galperin | A61B 1/00066 600/106 |
| 2016/0089127 | A1* | 3/2016 | Kirkemo | A61B 1/0052 606/110 |

* cited by examiner

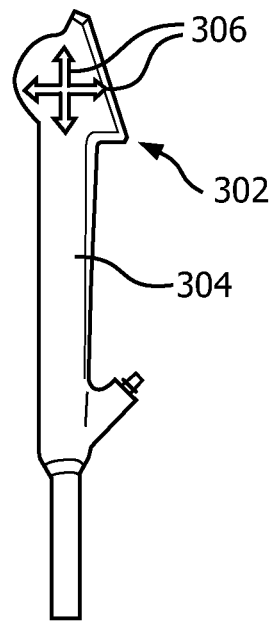
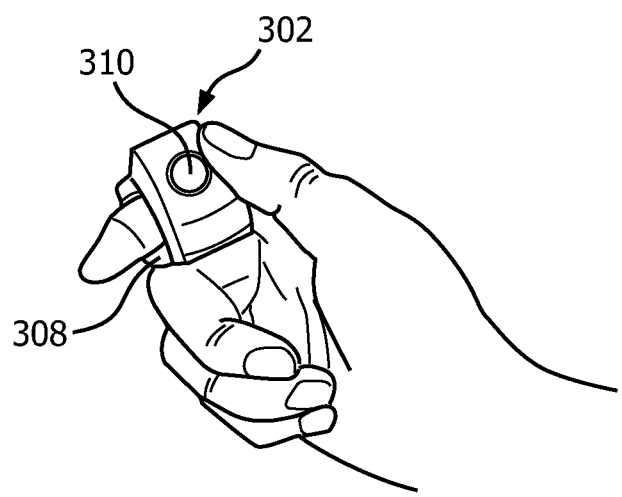
FIG. 4A  FIG. 4B
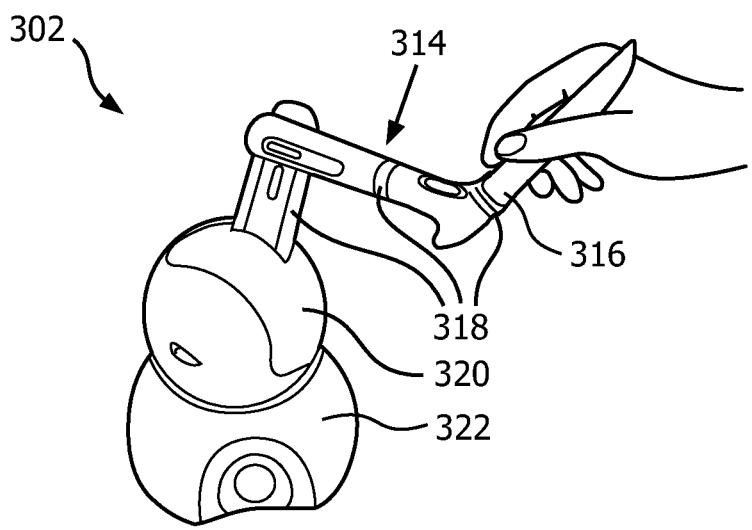
FIG. 4C

HANDHELD CATHETER DRIVER WITH ENDOSCOPE MOUNT UTILIZING FRICTION-DRIVEN WHEEL MECHANISM

CROSS-REFERENCE TO PRIOR APPLICATIONS

This application is the U.S. National Phase application under 35 U.S.C. § 371 of International Application Serial No. PCT/IB2015/057754, filed on Oct. 10, 2015, which claims the benefit of U.S. Application Ser. No. 62/067,477, filed on Oct. 23, 2014. This application is hereby incorporated by reference herein.

BACKGROUND

Technical Field

This disclosure relates to medical instruments and more particularly to a medical device driver that provides ergonomic features and improves procedural workflow.

Description of the Related Art

Catheter-assisted endoscopic interventions can significantly advance the navigation capability of endoscopes. However, endoscope manipulation can be cumbersome and requires multiple operators. This is more evident for catheter-assisted endoscope interventions where an increased number of instruments is needed. In one scenario, one doctor needs to operate the endoscope while the other operator employs a catheter and potentially an interventional tool. The cumbersome nature of endoscope use can also lead to fatigue of the operators.

For catheter-assisted endoscope intervention, at least three instruments are employed and many degrees of freedom (DOF) are required. This necessitates delicate coordination of multiple operators. The instruments and corresponding operation DOFs may include, e.g.: Endoscope: insertion, rotation, steering, holding the distal shaft for immobilization and guide, fluid flush; Catheter: insertion, rotation, deflection; Tool: insertion, rotation, deployment.

One of the major limitations of commercially available catheter drivers for endoscope-catheter-tool systems is that the systems completely change the workflow of traditional catheter operation. Another limitation includes the bulky design that usually utilizes more than 1-2 meters in length of space, is heavy and only allows ground mounting and control through teleoperation.

SUMMARY

In accordance with the present principles, an instrument driving mechanism includes an instrument drive assembly including a first set of wheels coupled to a first end portion and a second set of wheels coupled to a second end portion opposite the first end portion. The first set of wheels is configured to engage an elongated instrument therein such that a rotation plane of the first set of wheels is coplanar with a longitudinal axis of the instrument. The second set of wheels is configured to engage the elongated instrument therein such that a rotation plane of the second set of wheels is obliquely oriented with the longitudinal axis of the instrument wherein motion of the instrument is controlled by controlling rotations of the wheels. The instrument drive assembly mounts to a mounting position of a medical device that permits the instrument to pass therethrough and is configured to fix a position of the instrument drive assembly to enable positioning of the instrument.

Another instrument driving mechanism includes an instrument drive assembly including a first set of wheels coupled to a first end portion and a second set of wheels coupled to a second end portion opposite the first end portion. The first set of wheels is configured to engage an elongated instrument therein such that a rotation plane of the first set of wheels is coplanar with a longitudinal axis of the instrument, and the second set of wheels is configured to engage the elongated instrument therein such that a rotation plane of the second set of wheels is obliquely oriented with the longitudinal axis of the instrument wherein motion of the instrument is controlled by controlling rotations of the wheels. A joint is configured to mount the instrument drive assembly to a mounting position and permit the instrument to pass through the joint. The joint is configured to fix a position of the instrument drive assembly to enable positioning of the instrument.

Yet another instrument driving mechanism includes an instrument drive assembly including a first set of wheels coupled to a first end portion and a second set of wheels coupled to a second end portion opposite the first end portion. The first set of wheels is configured to engage a catheter therein such that a rotation plane of the first set of wheels is coplanar with a longitudinal axis of the catheter. The second set of wheels is configured to engage the catheter therein such that a rotation plane of the second set of wheels is obliquely oriented with the longitudinal axis of the catheter wherein fixation and motion of the catheter is controlled by controlling rotations of the wheels. A joint is configured to mount the instrument drive assembly to an endoscope and permit the catheter to pass through the joint into a working channel of the endoscope, the joint being configured to fix a position of the instrument drive assembly to enable positioning of the catheter. A telescopic stabilizer is configured to connect a handle of the catheter to the instrument drive assembly on an opposite side of for the joint. A user interface is configured to control the instrument drive assembly.

A method for driving an instrument includes positioning an instrument drive assembly on a mounting position on another device to mount the instrument drive assembly and permit an elongated instrument to pass through the other device; controlling motion of the instrument using the instrument drive assembly including a first set of wheels coupled to a first end portion and a second set of wheels coupled to a second end portion opposite the first end portion, the first set of wheels being configured to engage the instrument therein such that a rotation plane of the first set of wheels is coplanar with a longitudinal axis of the instrument, the second set of wheels being configured to engage the elongated instrument therein such that a rotation plane of the second set of wheels is obliquely oriented with the longitudinal axis of the instrument wherein fixation and motion of the instrument is controlled by controlling rotations of the wheels; and navigating the instrument using the first and second sets of wheels, which cooperate to provide a specific motion of the instrument.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein:

FIG. 4A is a diagram showing a user interface that includes control buttons on an endoscope in accordance with one embodiment;

FIG. 4B is a diagram showing a user interface that includes a strap with control buttons in accordance with one embodiment;

FIG. 4C is a diagram showing a user interface that includes an articulated haptic device in accordance with one embodiment.

DETAILED DESCRIPTION OF EMBODIMENTS

Figure 1A:
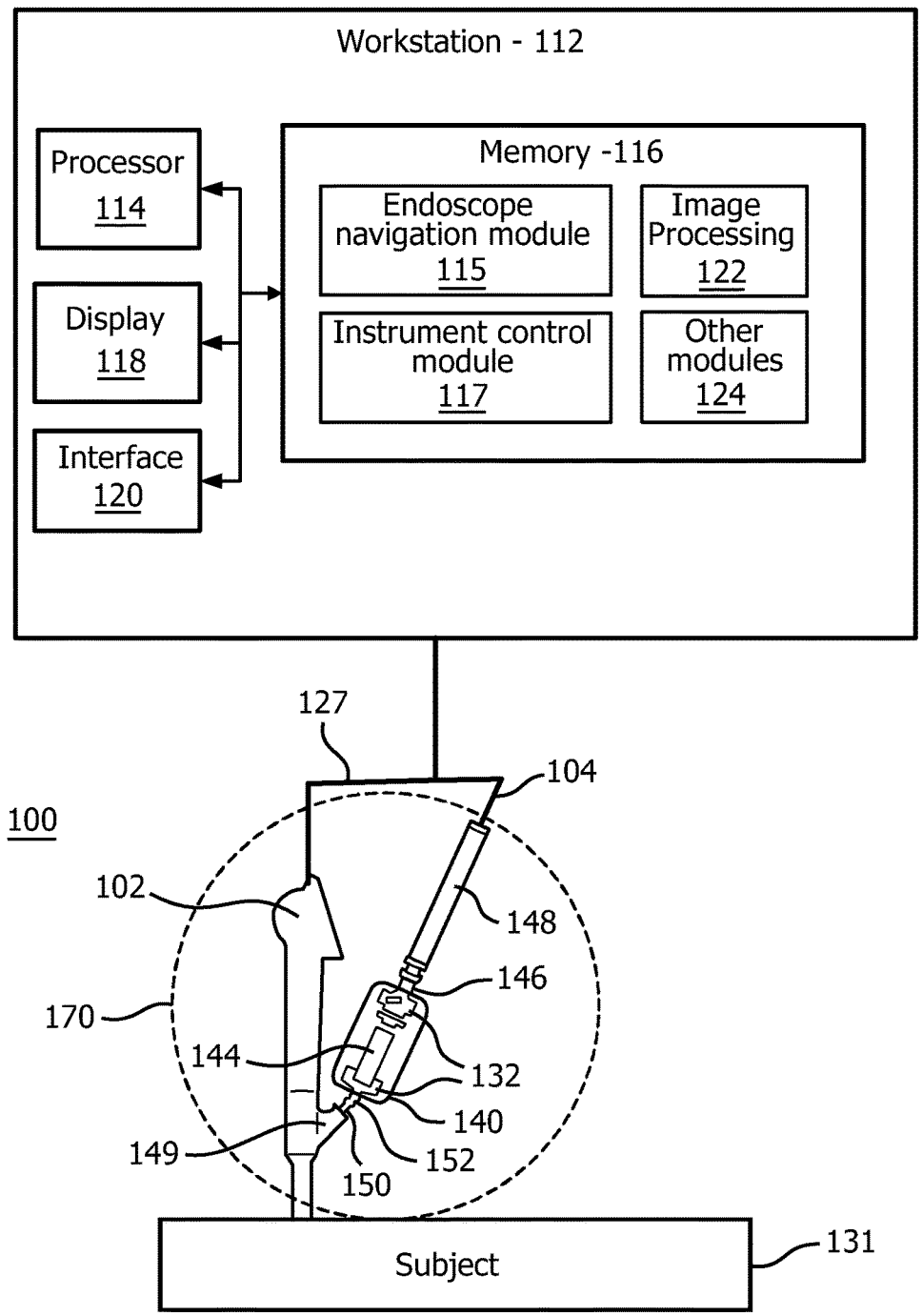
FIG. 1A is a block/flow diagram showing a system having an assembly for providing a catheter-assisted endoscopic intervention in accordance with one embodiment of the present principles.

In accordance with the present principles, systems and methods are described that overcome the shortcomings of conventional catheter-assisted endoscopic systems. Embodiments in accordance with the present principles provide lightweight friction drives and permit mounting to an endoscope with handheld operation of both the endoscope and a catheter driver. Precision motorized control of catheter insertion and rotation with closed-loop position feedback is also provided. In one embodiment, a compact endoscope-mount mechanism utilizes a friction wheel drive to control the catheter insertion and rotation motion. The catheter driver mechanism simplifies workflow, reduces operational personnel and enhances controllability of the catheter.

The present principles employ a differentially driven mechanism that has multiple friction wheels to cooperatively control catheter insertion and rotation. Since this mechanism is compact and lightweight, it can also be mounted on an endoscope working channel to aid with catheter manipulation. The mechanism may employ intelligent feedback from a multitude of sources to supply useful and precise actuation. Feedback sources may include, but are not limited to, force and position sensors, imaging information, motor driving torque, etc. The present embodiments streamline workflow, which has the potential to increase an adoption rate of the present procedures, and reduce the required personnel during an endoscopy/bronchoscopy procedure. The device can be used with an endoscope and employ quick attachment or detachment. The driver mechanism in accordance with the present principles can be configured to be directly operated by push buttons in combination with the endoscope, or it may be used as a slave driver mechanism to perform catheter navigation by remote control. These techniques can significantly simplify the workflow and can be used for a number of catheter-assisted endoscope procedures. Such procedures have increased in popularity as catheter access to smaller anatomy is being employed to aid in early diagnosis and therapy.

The present principles may be employed in combination with catheters or other instruments and endoscopes or the like to drive the motion of catheters through a joint connection to mount a catheter driver to the endoscope. The present principles also permit use of the endoscope to directly drive the motion of catheters by a single user. The catheter drive mechanism may be configured as slave drive mechanism to remotely control the catheter motion.

It should be understood that the present invention will be described in terms of catheter-based medical instruments; however, the teachings of the present invention are much broader and are applicable to any flexible, elongated instruments. In some embodiments, the present principles are employed in tracking or analyzing complex biological or mechanical systems. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Referring now to the drawings in which like numerals represent the same or similar elements and initially to FIG. 1A, a system 100 for performing a procedure, which employs an endoscope mount utilizing a friction-driven wheel mechanism for instrument control is illustratively shown in accordance with one embodiment. System 100 may include a workstation or console 112 from which a procedure is supervised, controlled and/or managed. Workstation 112 preferably includes one or more processors 114 and memory 116 for storing programs and applications. Memory 116 may store an endoscope navigation module 115 configured to interpret feedback signals and provide navigation directions for the placement and operation of a mounting device 102, such as an endoscope. The endoscope 102 may be manually controlled, although robotically controlled endoscopes may also be employed. The present principles provide the mounting device 102 with a mounting position 149 for securing another instrument 104.

Memory 116 may also store an instrument control module 117 configured to interpret feedback signals and control the placement and operation of the instrument 104. It should be understood that the endoscope 102 and the instrument 104 may include software and hardware (e.g., manual) controls and settings. In addition, although referred to as an endoscope 102 and instrument 104, these devices may include any instruments or devices that are employed in conjunction and should not be construed as limited to the examples given.

Modules 115 and 117 are configured to use the signal feedback (and any other available feedback) to position, reposition or perform other tasks with the endoscope 102 and the instrument 104, respectively. The instrument 104 may include a catheter, a guidewire, a probe, another endoscope, an electrode, a filter device, a balloon device, another medical component, etc.

The endoscope 102 and instrument 104 can communicate with their respective modules 115 and 117 through cabling 127 or wireless communications. The cabling 127 may include fiber optics, electrical connections, other instrumentation, etc., as needed.

In useful embodiments, workstation 112 includes modules to perform different tasks during a procedure. These modules may include an image processing module 122 to process images collected by the endoscope 102 or instrument 104. Other modules 124 may include application specific controls and measurements systems to control power, measure parameters, etc.

Workstation 112 preferably includes a display 118 for viewing internal images of a subject (patient) or volume 131. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112. For example, the user interface 120 allows the user to control the motion of the catheter 104. In one embodiment, the user interface 120 may include a strap with control buttons that wraps around the endoscope 102. Other examples of the user interface 120 are described herein.

In accordance with the present principles, a compact endoscope-mounted instrument drive mechanism or assembly 140 includes a friction wheel drive 132 to control insertion/retraction and rotation motion of instrument 104.

In a particularly useful embodiment, the instrument 104 includes a catheter that is positioned within a working channel of the endoscope 102. The friction wheel drive 132 includes friction wheel sets (136, 138, FIG. 2B) that are operated as a differential friction drive. The friction wheel drive sets include a first set (136) of friction wheels with a rotation plane coplanar with an insertion axis of the catheter 104. Note that the wheels themselves of the first set 136 have a rotation plane that is coplanar to the insertion axis of the catheter 104. A second set (138) of friction wheels includes an oblique angle to the insertion axis of the catheter 104.

Motion of the catheter 104 is determined by the coupled motion of the two wheel sets 136 and 138 in the instrument drive mechanism or assembly 140. When the oblique set 138 is driven, it imparts both a rotation force and a translational force on the catheter 104. If the coplanar set 136 is driven in the same direction, the catheter is advanced or retracted accordingly. If the set 136 is held fixed, the catheter 104 is prevented from moving along its axis. Encoders or other sensors (not shown) may be provided in motors 144 or with the wheel sets 136 and 138 to sense rotation and insertion motion of the catheter 104, and assist in closed-loop control of the catheter 104 to compensate for potential slippage of the wheels.

A telescopic stabilizer 146 (also known as a telescopic arm) may be employed to connect the catheter driver assembly 140 to a catheter handle 148, which protects a catheter shaft for the prevention of kinking. In addition, the use of the telescopic stabilizer 146 avoids the need for an extra person to operate the catheter 104.

The mounting position 149 may include or form a joint 150, e.g., a spherical joint, that may be employed to connect the endoscope 102 and the catheter driver assembly 140. An attachment mechanism 152 (e.g., a Luer lock) permits positioning of the catheter driver assembly 140 in different orientations while also permitting easy and quick detachment and attachment to the endoscope 102.

The catheter 104 preferably runs through the handle 148, through the telescopic stabilizer 146 and through the joint 150 into a base or mounting position (149) (e.g., on the endoscope 102, although other base mounts or positions may be employed). If the base position includes an endoscope 102, the catheter 104 (or other instrument) may run through a working channel of the endoscope 102.

In another embodiment, the catheter drive mechanism or assembly 140 can be employed independently of the endoscope 102 to directly control the motion of the catheter 104. For example, in a catheter-only navigation scenario, the friction-driven catheter drive mechanism 140 could operate independently to control an insertion and rotation motion of the catheter 104. The catheter 104 may be mounted, using the joint 150, to a port or other base. In one embodiment, the active catheter driver (140) mounts to the endoscope 102 and the instruments are employed together during a procedure.

The friction-driven catheter drive mechanism 140 can also be employed as a remotely controlled slave manipulator/mechanism, and the drive mechanism 140 could be table-mounted or ground-mounted and freestanding. In a particularly useful embodiment, the drive mechanism 140 is handheld and includes a light weight and smaller size to permit single user control and use of the device. In one embodiment, the drive mechanism 140 has a largest dimension of under about 4 inches, and preferably less.

Figure 1B:
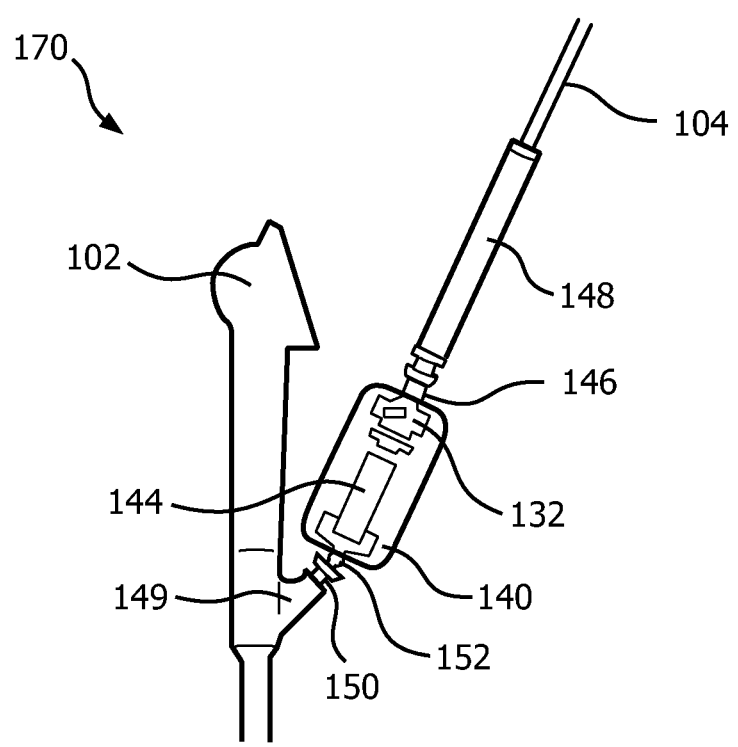
FIG. 1B is a diagram showing the catheter-assisted endoscopic intervention assembly in greater detail in accordance with the present principles.

A handheld assembly 170 may include the endoscope 102, the instrument drive mechanism 140, the instrument 104 and attachment devices (e.g., joint 150, lock 152, telescopic stabilizer 148, etc.). The assembly 170 is shown in greater detail in FIG. 1B.

Figure 2A:
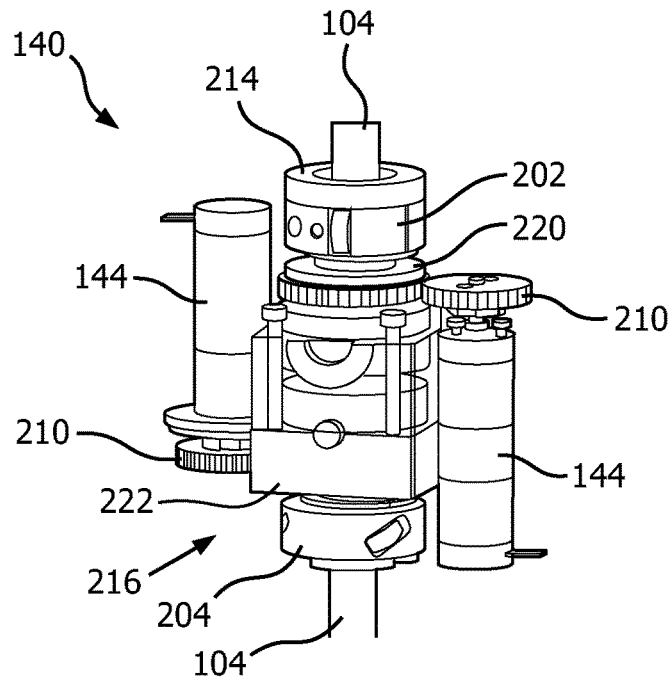
FIG. 2A is a diagram showing an instrument drive mechanism with its housing removed in accordance with one embodiment.
Figure 2B:
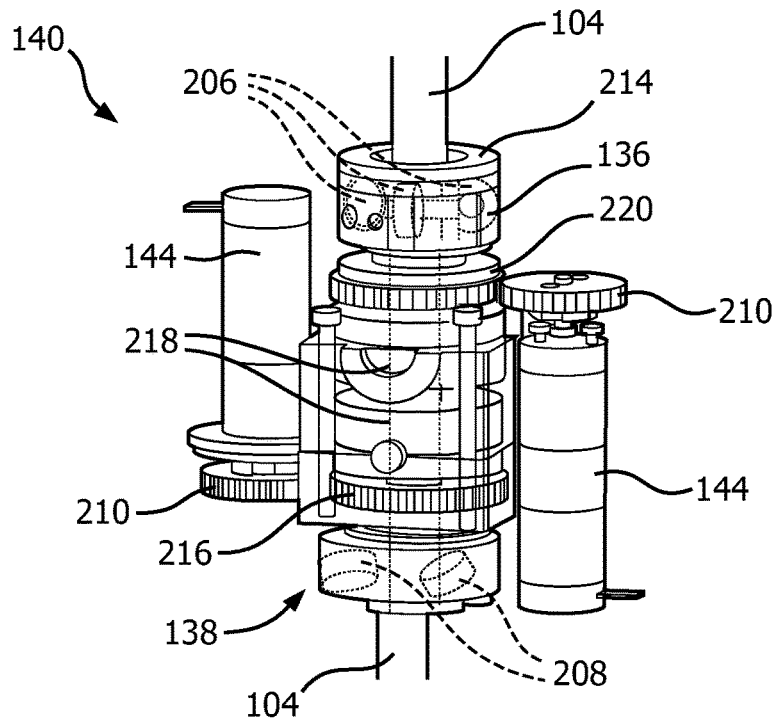
FIG. 2B is a diagram showing the instrument drive mechanism of FIG. 2A with bushing housings and assembly body housing removed to show internal parts in accordance with one embodiment.

Referring to FIGS. 2A and 2B, the catheter drive mechanism 140 is shown in greater detail with its housing removed. The mechanism 140 includes two rotary motors 144 to control the insertion and rotation of catheter 104 by friction. FIG. 2A shows external bushings 202 and 204. FIG. 2B shows wheels 206 and 208 in internal portions of the bushings 202 and 204. The catheter drive mechanism 140 includes a friction drive system used to control the catheter insertion and rotation. The catheter drive mechanism 140 includes the set 136 of friction wheels 206 with a rotation plane that is coplanar with the axis of the catheter 102. These wheels 206 (also known as straight wheels) are used to control the linear insertion motion of the catheter 104. In this configuration, three wheels (the minimum number of wheels) are employed to generate the friction, but multiple wheels (more than three) are also capable of driving the mechanism 140 with increased friction. The set 138 of friction wheels 208 has a rotation plane that is at an angle (oblique) with respect to the axis of the catheter 104. These wheels 208 (also referred to as oblique wheels) are employed to control the rotation motion of the catheter 104. In this configuration, three wheels 208 (the minimum number of wheels) are employed to generate the friction, but multiple wheels (more than three) are also capable of driving the mechanism 140 with increased friction.

The friction wheels 206, 208 may include different material selections, geometry, texture, mounting angles, etc. In some examples, steel, rubber, plastic or other material with low durameter may be used. The texture of the wheels 206, 208 may be knurled or include a microfinish to increase friction. More than three wheels may be employed to increase the friction as well.

Two rotary motors 144 drive the wheel-embedded bushings 202 and 204 through gears 210 for straight and oblique wheels, respectively. Two or more position sensing devices 214 (e.g., linear and rotary optical encoders) may be included to measure the insertion and rotation motion of the catheter 104 through reflected light, in a manner similar to an optical mouse. Other encoder systems may also be employed.

An assembly body 216 includes ball bearings 218 (FIG. 2B) and gears 220 to transfer and support stable motion of the wheels 206 and 208. The assembly body 216 is preferably covered by a housing 222 (FIG. 2A).

Figure 3A:
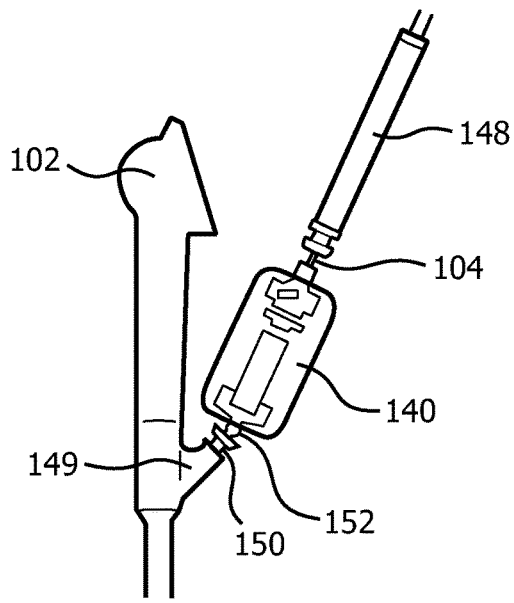
FIGS. 3A-3C show a spherical joint in different positions for adjusting a position of an instrument drive mechanism in accordance with the present principles.
Figure 3B:
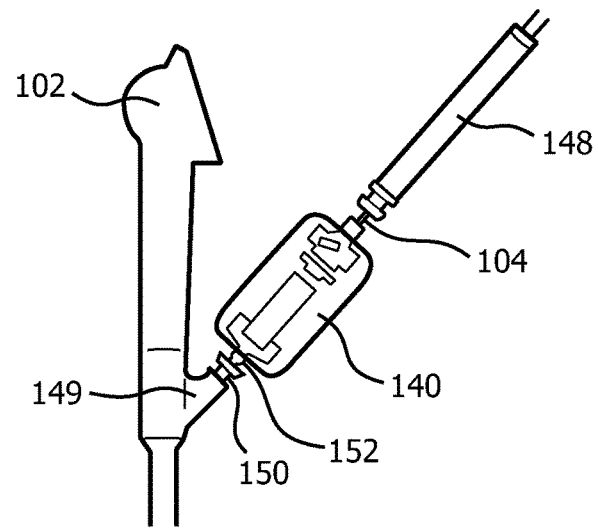
Figure 3C:
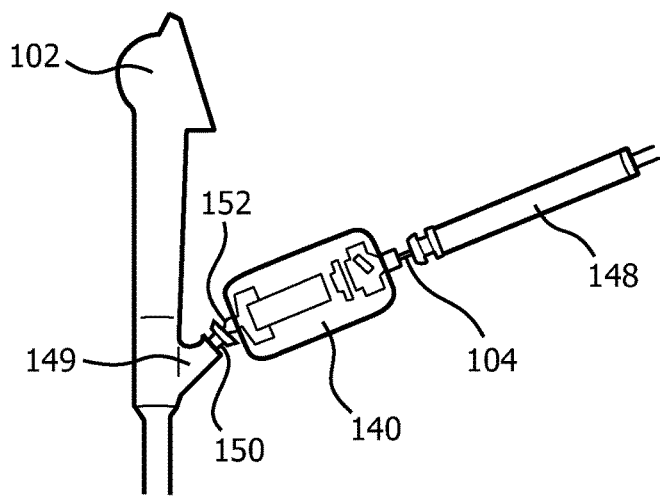

Referring to FIGS. 3A-3C, the system could optionally include a joint 150, e.g., a spherical joint that may include the attachment mechanism or lock 152, such as, e.g., a Luer lock. The spherical joint 150 connects a working channel of endoscope 102 and the catheter driver mechanism 140. The spherical joint 150 assists in orienting the friction drive mechanism 140 to any desired position. The spherical joint 150 may be lockable with a rotation knob that presses against the spherical ball in socket mechanism, although other mechanisms may also be employed.

The spherical joint 150 allows positioning the catheter driver mechanism or assembly 140 in different orientations as shown in FIGS. 3A, 3B and 3C. The spherical joint 150 is mounted to the endoscope 102 through the attachment mechanism 152, which aids with quick attachment and detachment. Since the spherical joint 150 can be adjusted to apply an appropriate amount of friction, the joint 150 is positionable in fixed orientations that can hold the catheter driver assembly 140.

Referring to FIGS. 4A-4C, alternative user interface controls 302 are illustratively depicted. The user interface controls 302 are configured to control the catheter drive assembly 140. In FIG. 4A, an endoscope handle 304 includes integrated buttons 306 for controlling the catheter drive assembly 140. Each button may control a direction or type of motion (e.g., translation versus rotation). Control integration with the endoscope handle permits the user to have push buttons on the handle of the endoscope 102 to manually control the catheter 104 driver without coming into physical contact with the catheter 104. One advantage of this would be a single user interface to operate both the endoscope 102 and the drive mechanism 140.

In FIG. 4B, a strap 308 with control buttons 310 is provided. The strap 308 may be wrapped around the endoscope 102 or be placed over a hand or finger of a user as a ring mouse with touch control. The strap 308 with control buttons 310 mounted on it may be attached to the endoscope handle. The strap 308 permits the user to position the control interface wherever desired. The control buttons 310 may include a joystick, buttons, knobs, a slide or any other physical control. The ring mouse with touch control may be configured to control the catheter driver's insertion and rotation motion, and this may be used in a wireless or wired configuration.

In FIG. 4C, another interface 302 may include an articulated haptic device 314. Device 314 may be employed to control the catheter drive assembly 140 and hence the catheter 104. The articulated haptic device 314 may be based on current sensing within the motors, wheel motion encoding, image feedback, etc. The articulated haptic device 314 may also be used to give a clinician tactile feedback through a handle 316 for the catheter contact force (e.g., against anatomical features). The articulated haptic device 314 includes links 318, which connect to a ball joint 320 on a base 322. Other configurations are also contemplated. This system (314) may or may not be directly connected to the endoscope handle.

Figure 5:
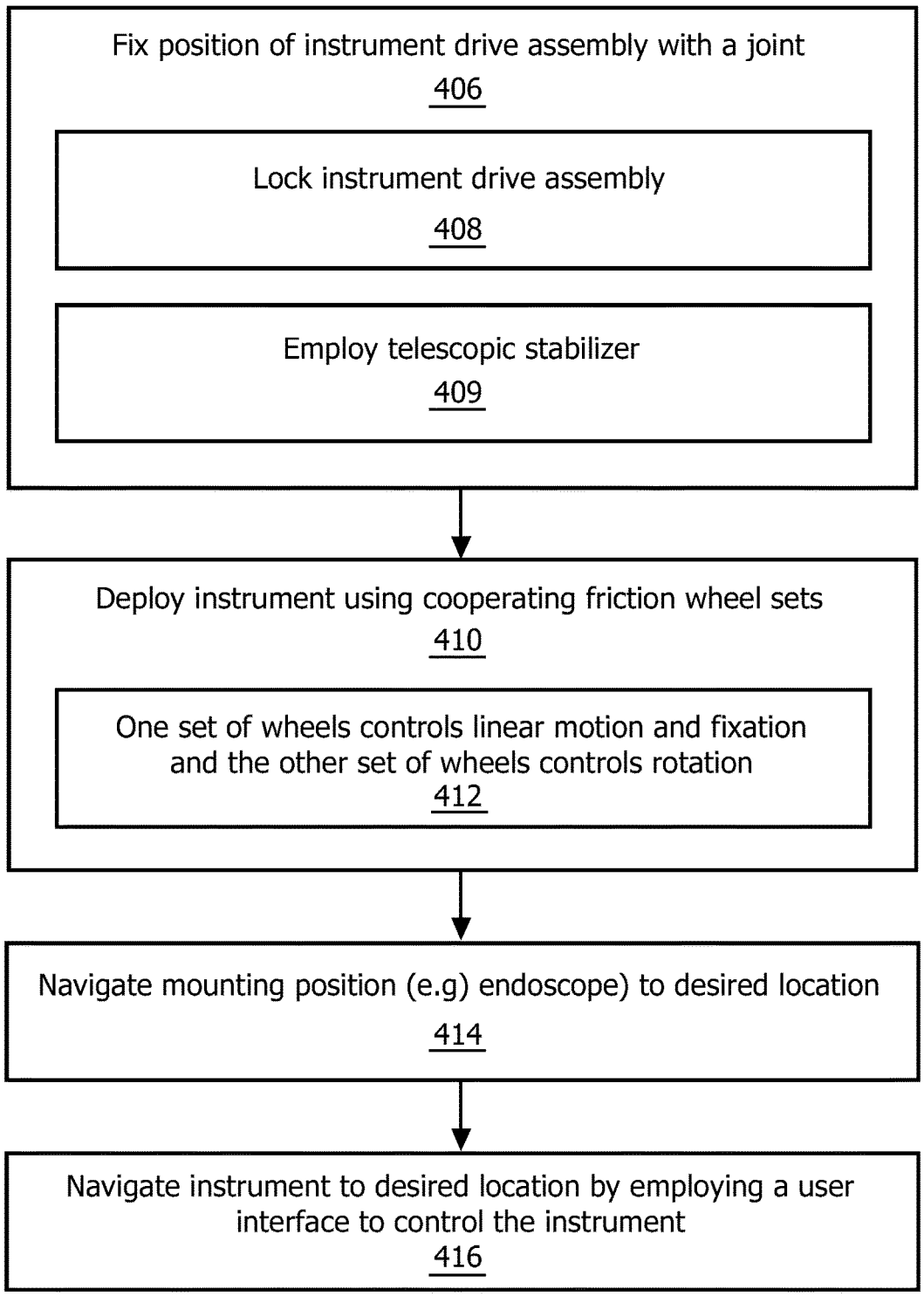
FIG. 5 is a flow diagram showing a method for driving an instrument in accordance with illustrative embodiments.

Referring to FIG. 5, a method for driving an instrument is shown in accordance with illustrative embodiments. In block 406, a position (e.g., rotation) of an elongated instrument drive assembly is fixed to enable positioning of the instrument using a joint configured to mount the instrument drive assembly to a mounting position and permit the instrument to pass through the joint. The joint may include a spherical joint, and the spherical joint may include a lock. The mounting position may be included on an endoscope and the instrument can be passed through the endoscope. In block 408, the position of the instrument drive assembly may be locked in a position by locking the joint. In block 409, a telescopic stabilizer may be employed to connect to and support a handle of the instrument, which may include a catheter.

In block 410, the instrument is deployed using first and second sets of wheels, which cooperate to provide a specific motion of the instrument. In block 412, the first set of wheels is controlled by a first motor to control linear motion and provide friction for the instrument, and the second set of wheels is controlled by a second motor to rotate the instrument.

Fixation and/or motion of the instrument, such as a catheter, is controlled using the instrument drive assembly, which includes the first set of wheels coupled to a first end portion and the second set of wheels coupled to a second end portion opposite the first end portion. The first set of wheels is configured to engage the instrument therein such that a rotation plane of the first set of wheels is coplanar with a longitudinal axis of the instrument, and the second set of wheels is configured to engage the elongated instrument therein such that a rotation plane of the second set of wheels is obliquely oriented with the longitudinal axis of the instrument wherein fixation and motion of the instrument is controlled by controlling rotations of the wheels.

In block 414, the mounting position which may include an endoscope or other medical device is navigated to a desired location (e.g., within a subject). In block 416, the instrument drive assembly may be controlled with a user interface to navigate the instrument to a desired location. The user interface may include a portable interface device that may be placed at or near the instrument drive assembly or disposed remotely from. The user interface may include an attachment mechanism to attach to an endoscope, to a body part of the user (or other) or any other object. The instrument drive assembly may be controlled through a user interface mounted on the endoscope. The user interface may include a specifically designed interface and may employ acoustic commands, haptic feedback, button or other device inputs, etc.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for handheld catheter driver with endoscope mount utilizing friction-driven wheel mechanism (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An instrument driving mechanism, comprising:
an instrument drive assembly including a first set of wheels coupled to a first end portion and a second set of wheels coupled to a second end portion opposite the first end portion, the first set of wheels being configured to engage an elongated instrument therein such that a rotation plane of the first set of wheels is coplanar with a longitudinal axis of the instrument, the second set of wheels being configured to engage the elongated instrument therein such that a rotation plane of the second set of wheels is obliquely oriented with the longitudinal axis of the instrument to provide both translational and rotational movement wherein motion of the instrument is controlled by controlling rotations of the wheels;
the instrument drive assembly mounts to a mounting position of a medical device that permits the instrument to pass therethrough and being configured to fix a position of the instrument drive assembly to enable positioning of the instrument.

2. The mechanism as recited in claim 1, wherein the first and second sets of wheels are controlled to cooperate to control motion of the instrument.

3. The mechanism as recited in claim 2, wherein the first set of wheels are controlled by a first motor to control linear motion and provide friction for the instrument and the second set of wheels are controlled by a second motor to rotate the instrument.

4. The mechanism as recited in claim 2, wherein the second set of wheels are controlled by a second motor to rotate the instrument and (i) driving the second set of wheels and the first set of wheels in the same direction causes the instrument to be advanced or retracted, and (ii) driving the second set of wheels with the first set of wheels held fixed prevents the instrument from being advanced or retracted.

5. The mechanism as recited in claim 1, wherein the mounting position forms a joint and the joint includes a lock to lock a position of the joint.

6. The mechanism as recited in claim 1, wherein the mounting position is included on the medical device, which includes an endoscope and the instrument is passed through the endoscope.

7. The mechanism as recited in claim 6, wherein the instrument drive assembly is controlled through a user interface mounted on the endoscope.

8. The mechanism as recited in claim 1, further comprising a user interface for controlling the instrument drive assembly by (i) using the first set of wheels to control linear insertion or retraction motion of the instrument and (ii) using the second set of wheels to control rotation motion of the instrument.

9. The mechanism as recited in claim 1, wherein the instrument includes a catheter and further comprising a telescopic stabilizer for connecting to and supporting a handle of the catheter.

10. The mechanism as recited in claim 1, wherein the first set of wheels includes at least three wheels and the second set of wheels includes at least three wheels.

11. An instrument driving mechanism, comprising:
an instrument drive assembly including a first set of wheels coupled to a first end portion and a second set of wheels coupled to a second end portion opposite the first end portion, the first set of wheels being configured to engage a catheter therein such that a rotation plane of the first set of wheels is coplanar with a longitudinal axis of the catheter, the second set of wheels being configured to engage the catheter therein such that a rotation plane of the second set of wheels is obliquely oriented with the longitudinal axis of the catheter to provide both translational and rotational movement wherein fixation and motion of the catheter is controlled by controlling rotations of the wheels;
a joint disposed adjacent at the first end portion and configured to mount the instrument drive assembly to an endoscope and permit the catheter to pass through the joint into a working channel of the endoscope, the joint being configured to fix a position of the instrument drive assembly to enable positioning of the catheter;
a telescopic stabilizer configured to connect a handle of the catheter to the instrument drive assembly adjacent the second end portion; and
a user interface configured to control the instrument drive assembly.

12. The mechanism as recited in claim 11, wherein the first and second sets of wheels are controlled to cooperate to control motion of the instrument.

13. The mechanism as recited in claim 12, wherein the first set of wheels are controlled by a first motor to control linear motion and provide friction for the instrument and the second set of wheels are controlled by a second motor to rotate the instrument.

14. The mechanism as recited in claim 12, wherein the second set of wheels are controlled by a second motor to rotate the instrument and (i) driving the second set of wheels and the first set of wheels in the same direction causes the instrument to be advanced or retracted, and (ii) driving the second set of wheels with the first set of wheels held fixed prevents the instrument from being advanced or retracted.

15. The mechanism as recited in claim 11, wherein the joint includes a spherical joint and the spherical joint includes a lock to lock a position of the joint.

16. The mechanism as recited in claim 11, wherein the user interface is mounted on the endoscope.

17. The mechanism as recited in claim 11, wherein the user interface includes a handheld portable instrument that is attachable to and detachable from objects.

18. The mechanism as recited in claim 11, wherein the first set of wheels includes at least three wheels and the second set of wheels includes at least three wheels.

19. A method for driving an instrument, comprising:
positioning an instrument drive assembly on a mounting position on another device to mount the instrument drive assembly and permit an elongated instrument to pass through the other device;
controlling motion of the instrument using the instrument drive assembly including a first set of wheels coupled to a first end portion and a second set of wheels coupled to a second end portion opposite the first end portion, the first set of wheels being configured to engage the instrument therein such that a rotation plane of the first set of wheels is coplanar with a longitudinal axis of the instrument, the second set of wheels being configured to engage the elongated instrument therein such that a rotation plane of the second set of wheels is obliquely oriented with the longitudinal axis of the instrument to provide both translational and rotational movement wherein fixation and motion of the instrument is controlled by controlling rotations of the wheels; and
navigating the instrument using the first and second sets of wheels, which cooperate to provide a specific motion of the instrument.

20. The method as recited in claim 19, wherein the first set of wheels includes at least three wheels and the second set of wheels includes at least three wheels.

* * * * *